(12) United States Patent
Uhde et al.

(10) Patent No.: US 11,596,484 B2
(45) Date of Patent: Mar. 7, 2023

(54) COMPENSATION OF TRACKING INACCURACIES

(71) Applicant: Brainlab AG, Munich (DE)

(72) Inventors: Jörg Uhde, Munich (DE); Manfred Weiser, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 17/630,790

(22) PCT Filed: Feb. 14, 2020

(86) PCT No.: PCT/EP2020/053989
§ 371 (c)(1),
(2) Date: Jan. 27, 2022

(87) PCT Pub. No.: WO2021/160294
PCT Pub. Date: Aug. 19, 2021

(65) Prior Publication Data
US 2022/0265363 A1    Aug. 25, 2022

(51) Int. Cl.
| | | |
|---|---|---|
| *G06K 9/00* | (2022.01) | |
| *A61B 34/20* | (2016.01) | |
| *A61B 34/00* | (2016.01) | |
| *A61B 90/50* | (2016.01) | |
| *G06T 7/70* | (2017.01) | |
| *A61B 6/12* | (2006.01) | |
| *A61B 6/00* | (2006.01) | |

(52) U.S. Cl.
CPC ............... *A61B 34/20* (2016.02); *A61B 6/12* (2013.01); *A61B 6/487* (2013.01); *A61B 34/25* (2016.02); *A61B 90/50* (2016.02); *G06T 7/70* (2017.01); *A61B 2034/2051* (2016.02); *A61B 2034/2055* (2016.02); *A61B 2034/2063* (2016.02); *A61B 2034/2065* (2016.02); *G06T 2207/10064* (2013.01); *G06T 2207/10116* (2013.01)

(58) Field of Classification Search
CPC ........... G06K 9/00; G16H 50/50; G61B 34/20
USPC ....... 382/100, 103, 106, 128–133, 154, 162, 382/168, 173, 181, 199, 219, 224, 254, 382/274, 276, 285–291, 305, 321; 600/424; 378/41; 703/11
See application file for complete search history.

(56) References Cited

U.S. PATENT DOCUMENTS

2005/0228270 A1    11/2005   Llyod et al.
2005/0281385 A1    12/2005   Johnson et al.
(Continued)

FOREIGN PATENT DOCUMENTS

WO    WO2014/197989 A1    12/2014

*Primary Examiner* — Seyed H Azarian
(74) *Attorney, Agent, or Firm* — Tucker Ellis LLP

(57) ABSTRACT

The disclosed method encompasses moving an object such as a medical device or instrument to a desired spatial position based on tracking data provided by a tracking system. Once it is determined from the tracking data that the object has reached the desired spatial position, a projection image is generated, which is registered with the desired spatial position and shows the object. Based on the image data, it is possible to verify whether the object has actually reached the desired position, or whether the object's actual position deviates from the desired position due to errors or inaccuracies, allowing measures to be taken to compensate for these errors or inaccuracies.

20 Claims, 4 Drawing Sheets

(56) References Cited

U.S. PATENT DOCUMENTS

| | | | |
|---|---|---|---|
| 2008/0154125 A1* | 6/2008 | Maier | G16H 50/50 |
| | | | 600/424 |
| 2009/0207971 A1* | 8/2009 | Uhde | A61B 6/547 |
| | | | 378/41 |
| 2010/0179418 A1* | 7/2010 | Mueller | A61B 34/20 |
| | | | 600/424 |
| 2014/0107390 A1* | 4/2014 | Brown | A61N 5/1045 |
| | | | 703/11 |
| 2016/0256223 A1* | 9/2016 | Haimerl | A61B 34/20 |
| 2018/0045512 A1* | 2/2018 | Uhde | A61B 34/20 |

* cited by examiner

COMPENSATION OF TRACKING INACCURACIES

RELATED APPLICATION DATA

This application is a national phase application of International Application No. PCT/EP2020/053989, filed Feb. 14, 2020, the contents of which are incorporated herein by reference.

FIELD OF THE INVENTION

The present invention relates to a computer-implemented method of compensating for tracking inaccuracies, a corresponding computer program, a computer-readable storage medium storing such a program and a computer executing the program, as well as a medical system comprising an electronic data storage device and the aforementioned computer.

TECHNICAL BACKGROUND

In the field of computer assisted surgery (CAS), radio-surgery and similar medical fields, determining the spatial position (spatial location and/or spatial orientation) of anatomical structures as well as of devices and instruments with respect to each other is a recurring object which is regularly taken over by so-called tracking systems, for example optical tracking systems, electromagnetic (EM)-tracking systems or ultrasound tracking systems. Such tracking systems are adapted to recognize so-called tracking markers that are rigidly attached to the objects the spatial position of which is to be determined or tracked over time. Before the spatial position of the actual object can be calculated on the basis of the detected spatial position of an attached tracking marker, a so-called registration procedure is necessary for most cases, which is to determine the spatial position of the actual object with respect to the spatial position of the tracking marker attached thereto.

As in any technical appliance, tracking procedures may be subject to errors resulting from measuring inaccuracies due to limited technical capabilities and/or unfavorable environmental conditions.

While during the tracking procedure as such, i.e. during the observation of the spatial position of objects over time based on the detection of tracking markers, possible tracking errors are usually less disruptive since the underlying sources of error such as ill-detection of markers and other detrimental environmental conditions basically remain the same over time, it is an initial positioning of objects preceding the actual tracking procedure where errors such as ill-detection of markers may have a heavy impact on the overall outcome of the medical procedure, and which may eventually lead to the spatial position of tracked objects being wrongly calculated.

The present invention has the object of providing an approach that compensates for errors or inaccuracies which in particular may occur during an initial positioning of objects.

The present invention can be used for any kind of Computer Assisted Surgery (CAS)-procedures e.g. in connection with an imaging device such as Loop-X®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses moving an object such as a medical device or instrument to a desired spatial position based on tracking data provided by a tracking system. Once it is determined from the tracking data that the object has reached the desired spatial position, a projection image is generated, which is registered with the desired spatial position and shows the object. Based on the image data, it is possible to verify whether the object has actually reached the desired position, or whether the object's actual position deviates from the desired position due to errors or inaccuracies, allowing measures to be taken to compensate for these errors or inaccuracies.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of compensating for tracking inaccuracies. The method comprises executing, on at least one processor of at least one computer (for example at least one computer being part of a navigation system), the following exemplary steps which are executed by the at least one processor.

In a (for example first) exemplary step, spatial image data is acquired which describes a three-dimensional representation of an anatomical body part. The three-dimensional representation may be obtained from an anatomical atlas, i.e. a statistical model of the anatomical body part. The three-dimensional representation may also be derived from a three-dimensional image of the anatomical body part, for example from a CT-image dataset or a MRI dataset, obtained via a CT-imaging apparatus or an MRI-apparatus, respectively. Further, the anatomical body part may be any body part comprising soft tissue and/or a bony structure. In a specific example relating to spine surgery, the anatomical body part may be represented by one or more vertebra(e).

In a (second) exemplary step, target position data is acquired which describes a desired spatial position of a trackable device with respect to the three-dimensional representation of the body part. In other words, a desired spatial position for a trackable device is defined relative to the anatomical body part, such that the trackable device is aligned with the anatomical body part as desired when it comes to rest in the desired spatial position. For example, such trackable device may be any medical or surgical object, device or instrument. In the specific example of spine surgery, the trackable device may be represented by a pedicle screw or a corresponding tool for handling the pedicle screw. In particular, the desired spatial position may be represented by a trajectory along which the pedicle screw has to be advanced with respect to a vertebra to reach a desired medical outcome.

In a (for example third) exemplary step, spatial registration data is acquired which describes a spatial registration of the three-dimensional representation of the body part together with the desired spatial position of the trackable device, and the actual body part. In other words, the three-dimensional representation of the body part along with the desired spatial position defined with respect to the representation is transferred into the same coordinate system as the actual/real anatomical body part. Thus, the desired spatial position of the trackable device is then known in real space with respect to the actual anatomical body part.

In a (for example fourth) exemplary step, tracking position data is acquired which describes current spatial position of the trackable device. The tracking position data is acquired via a tracking system.

In a (for example fifth) exemplary step and based on the acquired spatial registration data and the acquired tracking position data, control data is determined which describes instructions for positioning the trackable device at the desired position with respect to the body part. In other words, the tracking data acquired from the tracking system is then used to position the trackable device or instrument at the desired position. For example, the device or instrument may be moved automatically with the help of a motorized carrier or support structure instructed via at least one control signal derived from the control data, or may also be moved manually by a practitioner based on instructions which may be output, for example on a graphical user interface (GUI). Once the device or instrument has moved into the desired position, the tracking system finally indicates that the desired spatial position has been reached.

In a (for example sixth) exemplary step, imaging setup data is acquired which describes a positional setup of a projection imaging device for acquiring a two-dimensional projection image of the body part of the trackable device that has been positioned, based on the control data, at the desired spatial position. As it is the aim of the present approach to check for a correct positioning of the trackable device via a two-dimensional projection image, the geometric alignment of that image has to be known with respect to at least the desired spatial position of the trackable device. The necessary data describing the spatial position of the components of the projection imaging device may be acquired via the aforementioned or another tracking system which would necessitate tracking markers to be attached to the corresponding components, or via one or more sensors, for example positioning sensors integrated into the imaging device, which are suitable to provide data that indicates the spatial position of these components in a coordinate system. Further, known geometric properties of the imaging device such as a predefined distance between the emitter and the detector of an imaging device may deliver information on which the imaging setup data can also be based. In addition, the size and shape of the pixels on the detector can be taken into account.

In a (for example seventh) exemplary step, projection image data is acquired which describes the two-dimensional projection image. In this step the projection imaging device is controlled to generate at least one projection image showing the trackable device and the anatomical body part. Thus, the image shows the trackable device in a spatial position which the tracking system considers as the desired spatial position.

In a (for example eighth) exemplary step, position verification data is determined based on the imaging setup data, the projection image data and the spatial registration data, which describes a deviation of the spatial position of the trackable device as shown in the two-dimensional projection image, and the desired spatial position of the trackable device. In other words, this step is to compare the desired spatial position for the trackable device obtained via the tracking system, with the actual spatial position the trackable device has been moved to, based on the data acquired via the tracking system before the projection image was taken. If the spatial position of the trackable object is recognized by the tracking system correctly, i.e. the initial positioning is not subject to any (tracking) errors, the actual spatial position for the trackable object coincides with the desired spatial position. Otherwise, the image shows a deviation between the actual spatial position and the desired spatial position.

In a (for example ninth) exemplary step, position correction data is determined based on the position verification data, describing a positional compensation of the deviation in the spatial position of the trackable device. In case a deviation has been calculated in the foregoing step, appropriate measures can be taken to compensate for this deviation. For example, a transformation matrix can be calculated based on the determined deviation. This matrix can then be applied to the tracking data, such that the further tracking procedure is based on the correct spatial position of the trackable object. In the alternative, the matrix can also be applied to the actual position of the device; i.e. the real trackable device can be moved to the correct position, thereby compensating for the deviation.

According to a more specific example, the desired spatial position for the trackable device comprises at least one of:
- one single position or a plurality of spatial positions for the trackable device;
- a range of spatial positions for the trackable device;
- a trajectory for the trackable device.

If, for example, the trackable device or instrument, particularly a functional section thereof is rotationally symmetrical, the desired spatial position may comprise a plurality of spatial positions for the device or instrument around its symmetry axis. If, however, the trackable device or instrument has a more complex structure, the desired spatial position may be represented by a single spatial position. Further, a whole range of spatial positions may be defined as desired for the trackable device, as it may for example be sufficient for the device to be aligned within or parallel to a predefined plane. Moreover, a straight line or trajectory may be defined as a desired position as it may be sufficient when the device or instrument is aligned with that straight or trajectory. This may be the case for elongated instruments or devices such as stylets, catheters, pointer instruments and even nails and screws.

In a further, more specific example, acquiring projection image data includes acquiring at least two projection images having substantially the same imaging direction, particularly wherein separate projection images are acquired for the body part and the trackable device, respectively, specifically wherein the projection images are confined to a projection of the body part and the trackable device, respectively.

As one single projection image may not be sufficient to cover both, the trackable device and the anatomical body part, such image could be composed of two or more single projection images. In this respect, it is however important to note that these images need to have substantially the same imaging direction. While a small deviation between the respective imaging directions may be tolerable for the intended purpose of the images, a larger deviation would compromise the intended outcome, namely to accurately determine a possible deviation between the desired and the actual spatial position of a trackable device.

Moreover, the projection image(s) may be confined to the projection of the anatomical body part and/or the trackable device, for example by using a collimator of the imaging device, in order to keep the radiation exposure for the patient as low as possible. Two or more of these confined or "collimated" images may then be combined to a single projection image, particularly wherein the emitter and the detector maintain their position for the images acquired, but wherein the collimator configuration is different for different images, i.e. confined to projections of anatomical structures or trackable devices contained in the respective images. Further, it may be desirable for some cases to omit radiation sensitive parts of the patient's anatomy as well as medical appliances which may for example cause image artifacts.

In a further example, acquiring projection image data involves acquiring at least two projection images having different imaging directions, wherein position correction data is determined in different image planes of the projection images acquired. While a single two-dimensional projection image is sufficient to determine possible deviations of the trackable device within the image plane, i.e. should sufficiently reveal two translational and one rotational degree of freedom of possible deviations, a further image taken in another spatial direction may help in revealing most of the remaining degrees of freedom for possible deviations. In the case of x-ray-images being generated, this however comes with additional radiation exposure for the patient, which may be undesired in some cases.

Once the projection image is generated, a possible deviation between the desired and the actual spatial position for the trackable device is only shown in the projection image, without being processable for the tracking system or a navigation system. For that reason, the revealed deviation(s) need(s) to be transformed from the image plane into a three-dimensional coordinate system, for example the tracking system's coordinate system.

Thus, in another specific example, determining position verification data includes:
  matching a projection of the body part in the projection image to a two-dimensional representation of the body part reconstructed from the spatial image data; and/or
  matching a projection of the trackable device in the projection image to a two-dimensional representation of the trackable device reconstructed from data describing the three-dimensional shape of the trackable device.

With the matching of the body part projections, the desired spatial position, e.g. the planned trajectory for the trackable device, is determined within the image plane, the spatial orientation of which can be determined within the coordinate system of the spatial image data. Thus, the desired spatial position may then also be transformed into the three-dimensional real world coordinate system of the actual anatomical body part and/or the three-dimensional coordinate system of the tracking system. The same applies to the projection of the trackable device. Thus, it is possible to calculate the deviation between the desired spatial position and the actual spatial position of the trackable device within the image plane, the orientation of which is known within the three-dimensional coordinate system assigned to the actual anatomical structure or to the tracking system, or within any other three-dimensional coordinate system registered thereto.

In order to determine the full spatial position of the image plane within the three-dimensional coordinate system of the anatomical structure and/or of the tracking system, which additionally includes the "depth-information", i.e. the position of the image plane along the imaging direction within the three-dimensional coordinate system, determining position verification data may involve a transformation of positional data from the two-dimensional dimensional image space of the projection image into the three-dimensional space of the body part, particularly wherein the transformation is based on the desired spatial position and/or the current spatial position of the trackable device in the three-dimensional space of the body part derived from the spatial registration data and the tracking position data, respectively.

Since the desired spatial position as well as the actual spatial position of the trackable device is already known within the three-dimensional coordinate system, this information can be used to determine the spatial position of the image plane along the imaging direction. Possible positional errors are negligible here.

In a further example, acquiring imaging setup data is based on the spatial registration data and/or the tracking position data, particularly wherein a positional setup of the projection imaging device is selected from a plurality of possible positional setups, which is expected to provide valuable information about possible spatial deviations of the trackable device from a desired spatial position, specifically wherein a positional setup of the projection imaging device is selected that provides a projection image having an image plane substantially parallel to a desired spatial direction of the trackable device and/or an expected spatial deviation of the trackable device.

In other words, the projection imaging device is positioned with respect to the actual spatial position and/or the desired spatial position for the trackable device such that a single projection image acquired delivers the best information possible about a possible deviation. For example, if a translational deviation is of interest or is expected in a certain spatial direction, a projection imaging device should be positioned such that the imaging direction is, at best, perpendicular to the direction of that deviation. In case of rotational deviation is of interest or is expected, the imaging direction should, at best, run parallel to the axis of rotation.

Further, the step of acquiring imaging setup data may also be based on the spatial position of at least one object and/or at least one volume that needs to be avoided by the projection path of the projection image. For example, the projection imaging device may be positioned such that radiation sensitive parts of the patient's anatomy are not subject to radiation emitted by the projection imaging device. The same may apply to any medical appliances positioned adjacent to the trackable device and the anatomical body part, which may cause artifacts in the images acquired.

After an undesired deviation between the desired spatial position and the actual spatial position of the trackable device is revealed by the approach as described above, a positional compensation of the deviation of the trackable device's spatial position may be
  applied to the spatial position of the trackable device in the three-dimensional space, particularly by correspondingly controlling a motorized support structure holding the trackable device; or
  applied to the spatial position of the trackable instrument as detected by a medical tracking system, particularly to the spatial position of a representation of the trackable device as shown on a graphical user interface of a medical navigation system.

Thus, particularly if the trackable device or instrument is held via mechanical support structure such as a motorized articulated support arm, the actual spatial position of the trackable device can be corrected to coincide with the desired spatial position. On the other hand, particularly if the trackable device is held by a practitioner, the spatial position of the instrument representation as shown on a display may be corrected to the actual spatial position such that the practitioner may then undertake the necessary adjustments to finally the bring the trackable device into the desired spatial position.

For example, the at least one projection image as described above may be acquired via at least one of fluoroscopy and radiography. In one embodiment, the at least one projection image may be acquired via fluoroscopy. In a second embodiment, the at least one projection image may be acquired via radiography. In a third embodiment, the at least one projection image may be acquired by fluoroscopy and radiography.

Further, the tracking position data may be acquired via a medical tracking system selected from the group consisting of:
- an optical tracking system, particularly an IR-tracking system;
- an electromagnetic (EM)-tracking system;
- an ultrasound-tracking system;
    - which is adapted to determine the spatial position of one or more tracking markers coupled to the trackable device, particularly wherein the tracking system or an additional tracking system is further adapted to determine the spatial position of at least:
- the anatomical body part;
- the projection imaging device, particularly an emitter and/or a detector thereof.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect;
b) at least one electronic data storage device (3) storing at least the spatial image data; and
c) a trackable device (4) for carrying out a medical procedure on the patient, wherein the at least one computer is operably coupled to.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant or tracking marker in order to fasten it to an anatomical structure or a step of fastening the medical implant or tracking marker to the anatomical structure or a step of preparing the anatomical structure for having the medical implant or tracking marker fastened to it. More particularly, the invention does not involve or in particular comprise or encompass any surgical or therapeutic activity.

Use of the Device or System

The present invention also relates to the use of the device/system or any embodiment thereof for conducting a medical procedure Definitions In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy.

In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Marker Holder

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Pointer

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Imaging Geometry

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to a plane (for example, the plane of an x-ray detector). With respect to the connection between three-dimensional analysis objects and two-dimensional analysis images as defined by the imaging geometry, reference is made for example to the following publications:
1. "An Efficient and Accurate Camera Calibration Technique for 3D Machine Vision", Roger Y. Tsai, Proceedings of the IEEE Conference on Computer Vision and Pattern Recognition. Miami Beach, Florida, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic image processing for computer-aided orthopaedic surgery", Yaniv Z., Joskowicz L., Simkin A., Garza-Jinich M., Milgrom C. (1998) Fluoroscopic image processing for computer-aided orthopaedic surgery. In: Wells W. M., Colchester A., Delp S. (eds) Medical Image Computing and Computer-Assisted Intervention—MICCAI'98. MICCAI 1998. Lecture Notes in Computer Science, vol 1496. Springer, Berlin, Heidelberg.
4. EP 08 156 293.6
5. U.S. 61/054,187

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
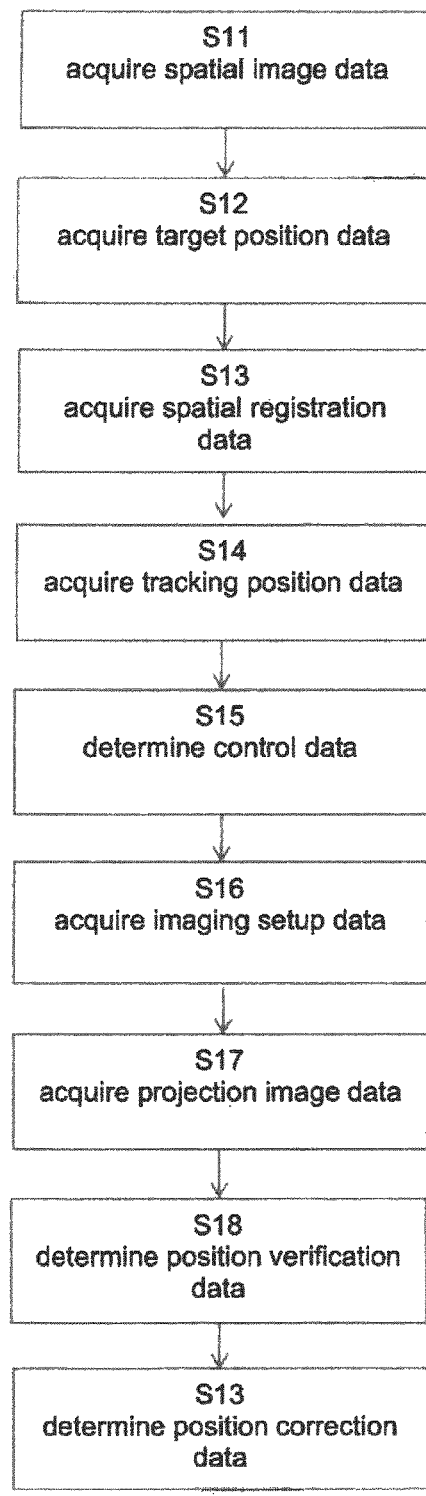
FIG. 1 illustrates a flow-diagram of basic method-step according to the first aspect of the present invention, which may be performed by a computer in accordance with the fourth aspect of the present invention.

FIG. 1 illustrates the basic steps of the method according to the first aspect as described in more detail further above.

Figure 2:
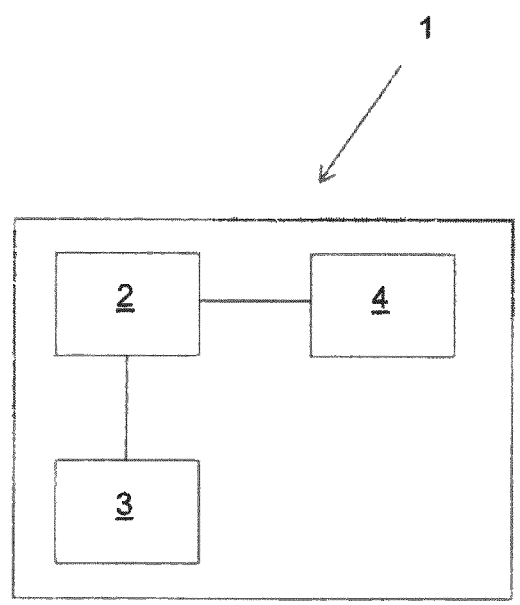
FIG. 2 shows a schematic illustration of the system according to the fifth aspect of the present invention.

FIG. 2 shows a schematic illustration of the medical system 1 according to the fifth aspect. The system is in its entirety identified by reference sign 1 and comprises a computer 2, an electronic data storage device (such as a hard disk) 3 for storing at least the spatial image data and a tracking system 4 (e.g. an optical IR tracking system). The components of the medical system 1 have the functionalities and properties explained above.

Figure 3:
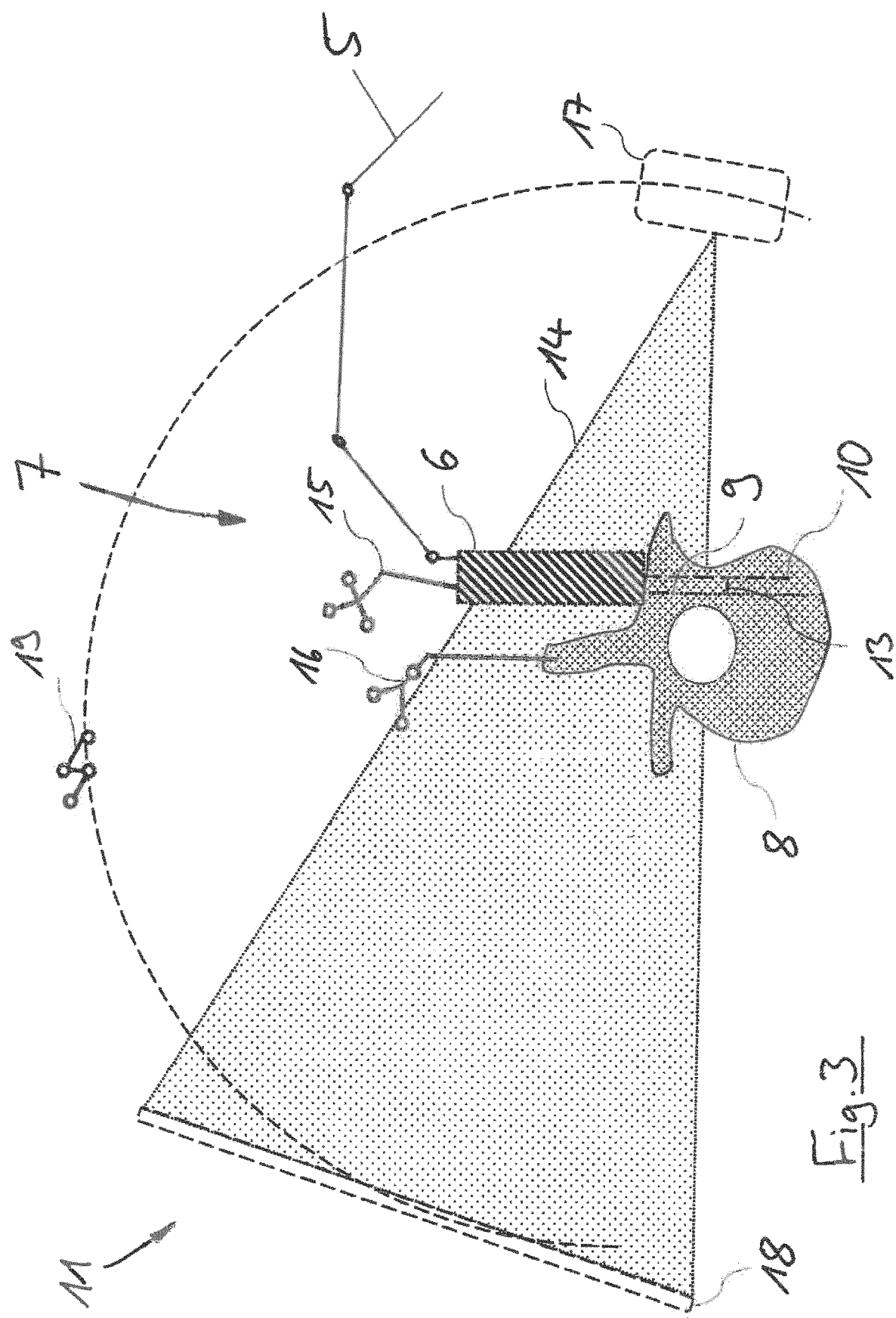
FIG. 3 shows an exemplary setup of a projection imaging device with respect to an anatomical body part and a trackable device.
Figure 4:
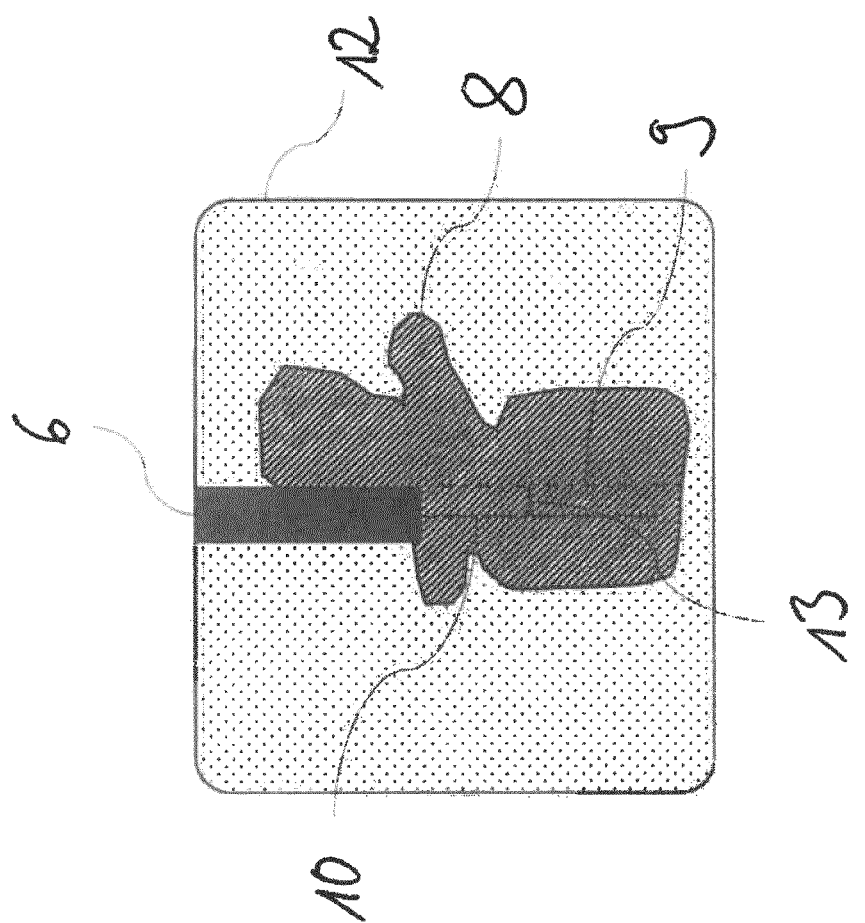
FIG. 4 shows a display illustrating the positional setup of FIG. 3.

FIG. 3 shows an exemplary positional setup of a projection imaging device 11 having an emitter 17 and a detector 18, that generates an x-ray-image 12 (cf. FIG. 4) of a vertebra 8 and an instrument 6.

A previous imaging acquisition procedure provides a three-dimensional image dataset, for example CT-dataset or an MR-dataset, of the vertebra 8. A desired trajectory 9 is defined by a practitioner with respect to the three-dimensional representation of the vertebra 8, along which a pedicle screw (not shown) is planned to be advanced into the right pedicle of the vertebra 8 with the help of instrument-tool 6.

In order to determine its spatial position, tool 6 is provided with an optical marker array 15 that can be detected in space by the optical tracking system 4 (cf. FIG. 2). In case an initial positioning of tool 6 along the desired trajectory 9 is inaccurate, the tracking system 4 deliver inaccurate results about the spatial position of tool 6. In the illustrative example shown in FIG. 3, the tracking system 4 locates tool 6 as aligned along the desired trajectory 9, even though tool 6 is actually aligned with trajectory 10. Without the inventive approach being applied, tracking system 4 would locate tool 6 at a position that deviates from its actual position by a shift 13.

In order to compensate for this possible inaccuracy, a specific example of the inventive approach is performed as follows:

Based on the information obtained so far, including the tracking information detained via the tracking system 4, the motorized support structure 5 is controlled to move tool 6 to align along the desired trajectory 9.

After the tracking system 4 indicates that tool 6 is aligned along the desired trajectory 9, the projection imaging apparatus 11 is controlled to acquire a projection image of the vertebra along with the tool 6. In order to obtain an image that is meaningful in regards to a possible but yet unknown deviation 13, the emitter 17 and the detector 18 are controlled to align in an imaging direction that is, as far as possible, perpendicular to the desired trajectory 9. The spatial positions of both, the emitter 17 and the detector 18 is recognized by the tracking system 4 via tracking markers 19.

The generated image including the two-dimensional representations of the vertebra 8 and the tool 6 then needs to be transformed into the three-dimensional coordinate system of the tracking system 4 in order to evaluate possible deviations of the tools 6 actual trajectory 10 from the desired trajectory 9. It is important to note here that possible deviations between the actual trajectory 10 and the desired trajectory 9 are rather small as compared to the distance between the emitter 17 and the vertebra 8/tool 6, as well as to the distance between the detector and the vertebra 8/tool 6. The expression "image plane" as used herein is to define an image plane between the emitter 17 and the detector 18, which is perpendicular to the imaging trajectory and contains the spatial location of the trackable device 7 (e.g. the tool 6) and/or of the body part 8 (e.g. the vertebra 8), particularly a predefined section of the trackable device 7 and/or of the body part 8, such as an instrument tip or a landmark of the vertebra 8. The spatial position of the image plane along the imaging trajectory can therefore be calculated on the basis of the tool's 6 or vertebra's 8 spatial position. Because of the basic proportionality theorem, possible tracking inaccuracies will have, if at all, only little effect here.

With the image 12 and its content being transformed into the three-dimensional coordinate system based on the basic proportionality theorem, the possible deviation 13 within the image plane can then be calculated in the three-dimensional coordinate system.

Based on this information, the motorized support arm 5 can be controlled to compensate for the detected deviation for the rest of the tracking procedure by a translational shift of tool 6 until it aligns with the desired trajectory 9. The further tracking procedure can then be based on the corrected tracking information.

The invention claimed is:

1. A computer-implemented medical method of compensating for tracking inaccuracies, the method comprising:
    a) acquiring a three-dimensional image dataset comprising spatial image data that describes a three-dimensional representation of an associated physical anatomical body part;
    b) acquiring target position data that describes in three-dimensional image dataset a desired spatial position of an associated trackable device with respect to the three-dimensional representation of the associated physical anatomical body part;
    c) acquiring spatial registration data that describes a spatial registration of the three-dimensional representation of the associated physical anatomical body part together with the desired spatial position of the associated trackable device in the three-dimensional image dataset with the associated physical anatomical body part;
    d) acquiring tracking position data that describes a current spatial position of the associated trackable device;
    e) determining control data based on the spatial registration data and the tracking position data, wherein the control data describes one or more instructions for positioning the associated trackable device at the desired spatial position with respect to the associated physical anatomical body part;
    f) acquiring imaging setup data that describes a positional setup of an associated projection imaging device operable to acquire a two-dimensional projection image of the associated physical anatomical body part and of the associated trackable device having been positioned, based on the control data, at the desired spatial position;

g) acquiring projection image data that describes the two-dimensional projection image;

h) determining position verification data based on the imaging setup data, the projection image data and the spatial registration data, wherein the position verification data describes a deviation between:

the current spatial position of the associated trackable device as shown in the two-dimensional projection image; and the desired spatial position of the associated trackable device; and i) determining position correction data based on the position verification data, the position correction data comprising a transformation matrix describing a positional compensation of the deviation of the associated trackable device between the current spatial position and the desired spatial position.

2. The method according to claim 1, wherein the desired spatial position comprises at least one of:

one single spatial position or a plurality of spatial positions for the associated trackable device;

a range of spatial positions for the associated trackable device; and/or a trajectory for the associated trackable device.

3. The method according to claim 1, wherein acquiring projection image data includes acquiring at least two projection images having the same imaging direction.

4. The method according to claim 3, wherein separate projection images are acquired for the associated physical anatomical body part and the associated trackable device, respectively, and wherein the projection images are confined to a projection of the associated physical anatomical body part and the associated trackable device, respectively.

5. The method according to claim 1, wherein acquiring projection image data involves acquiring at least two projection images having different imaging directions, wherein position correction data is determined in different image planes of the projection images acquired.

6. The method according to claim 1, wherein determining position verification data includes at least one of:

matching a projection of the associated physical anatomical body part in the projection image to a two-dimensional representation of the associated physical anatomical body part reconstructed from the spatial image data; and/or matching a projection of the associated trackable device in the projection image to a two-dimensional representation of the associated trackable device reconstructed from data describing the three-dimensional shape of the associated trackable device.

7. The method according to claim 1, wherein determining position verification data involves a transformation of positional data from the two-dimensional image space of the projection image into the three-dimensional space of the associated physical anatomical body part.

8. The method according to claim 7, wherein the transformation is based on at least one of the desired spatial position and the current spatial position of the associated trackable device in the three-dimensional space of the associated physical anatomical body part derived from the spatial registration data and the associated tracking position data, respectively.

9. The method according to claim 1, wherein acquiring imaging setup data is based on at least one of the spatial registration data and the tracking position data, wherein a positional setup of the projection imaging device is selected from a plurality of possible positional setups, which is expected to provide information about possible spatial deviations of the associated trackable device from a desired spatial position.

10. The method according to claim 9, wherein selecting the positional setup of the projection imaging device is further based on the spatial position of at least one of an object and a volume that needs to be avoided by the projection path of the projection image.

11. The method according to claim 9, wherein a positional setup of the projection imaging device is selected that provides a projection image having an image plane parallel to at least one of the spatial direction of a desired spatial position of the associated trackable device and of the expected spatial deviation of the associated trackable device.

12. The method according to claim 1, wherein the positional compensation of the deviation of the associated trackable device spatial position is applied to:

the spatial position of the associated trackable device in the three-dimensional space by correspondingly controlling a motorised support structure holding the associated trackable device or instrument; or the spatial position of the associated trackable device as detected by an associated medical tracking system wherein the spatial position of a representation of the associated trackable device is shown on a graphical user interface of an associated medical navigation system.

13. The method according to claim 1, wherein the at least one projection image is acquired via at least one of fluoroscopy and/or radiography.

14. The method according to claim 1, wherein the tracking position data is acquired via an associated medical tracking system selected from the group consisting of:

an optical tracking system, particularly an IR-tracking system;

an electromagnetic (EM)-tracking system; and/or an ultrasound-tracking system, wherein the associated medical tracking system is adapted to determine the spatial position of one or more tracking markers coupled with the associated trackable device.

15. The method according to claim 14, wherein the tracking system or an additional tracking system is further adapted to determine the spatial position of at least one of:

The associated physical anatomical body part; and/or the projection imaging device emitter or detector.

16. A non-transitory computer-readable medium that when executed by a computer, causes the computer to perform a computer-implemented medical method of compensating for tracking inaccuracies, the method comprising:

a) acquiring a three-dimensional image dataset comprising spatial image data that describes a three-dimensional representation of an associated physical anatomical body part;

b) acquiring target position data that describes in three-dimensional image dataset a desired spatial position of an associated trackable device with respect to the three-dimensional representation of the associated physical anatomical body part;

c) acquiring spatial registration data that describes a spatial registration of the three-dimensional representation of the associated physical anatomical body part together with the desired spatial position of the associated trackable device in the in three-dimensional image dataset with the associated physical anatomical body part;
d) acquiring tracking position data that describes a current spatial position of the associated trackable device;
e) determining control data based on the spatial registration data and the tracking position data, wherein the control data describes one or more instructions for positioning the associated trackable device at the desired spatial position with respect to the associated physical anatomical body part;
f) acquiring imaging setup data that describes a positional setup of an associated projection imaging device operable to acquire a two-dimensional projection image of the associated physical anatomical body part and of the associated trackable device having been positioned, based on the control data, at the desired spatial position;
g) acquiring projection image data that describes the two-dimensional projection image;
h) determining position verification data based on the imaging setup data, the projection image data and the spatial registration data, wherein the position verification data describes a deviation between:
the current spatial position of the associated trackable device as shown in the two-dimensional projection image; and
the desired spatial position of the associated trackable device; and
i) determining position correction data based on the position verification data, the position correction data comprising a transformation matrix describing a positional compensation of the deviation of the associated trackable device between the current spatial position and the desired spatial position.

17. A medical system, comprising:
a) at least one computer comprising a processor and a non-transitory computer readable storage medium storing a program executable by the processor to:
acquire a three-dimensional image dataset comprising spatial image data that describes a three-dimensional representation of an associated physical anatomical body part;
acquire target position data that describes in three-dimensional image dataset a desired spatial position of an associated trackable device with respect to the three-dimensional representation of the associated physical anatomical body part;
acquire spatial registration data that describes a spatial registration of the three-dimensional representation of the associated physical anatomical body part together with the desired spatial position of the associated trackable device in the in three-dimensional image dataset with the associated physical anatomical body part;
acquire tracking position data that describes a current spatial position of the associated trackable device;
determine control data based on the spatial registration data and the tracking position data, wherein the control data describes one or more instructions for positioning the associated trackable device at the desired spatial position with respect to the associated physical anatomical body part;
acquire imaging setup data that describes a positional setup of an associated projection imaging device operable to acquire a two-dimensional projection image of the associated physical anatomical body part and of the associated trackable device having been positioned, based on the control data, at the desired spatial position;
acquire projection image data that describes the two-dimensional projection image;
determine position verification data based on the imaging setup data, the projection image data and the spatial registration data, wherein the position verification data describes a deviation between:
the current spatial position of the associated trackable device as shown in the two-dimensional projection image; and
the desired spatial position of the associated trackable device; and
determining position correction data based on the position verification data, the position correction data comprising a transformation matrix describing a positional compensation of the deviation of the associated trackable device between the current spatial position and the desired spatial position;
b) at least one electronic data storage device storing at least the spatial image data; and
c) a tracking system for acquiring at least the associated tracking position data, and comprising an interface for transmitting the control data, wherein the interface is connected to the associated projecting imaging device to acquire the imaging setup data.

18. The medical system according to claim 17, further comprising the associated trackable device configured to carry out a medical procedure on the patient, wherein the at least one computer is operably coupled with:
the at least one electronic data storage device for acquiring, from the at least one electronic data storage device, at least the spatial image data; and
the associated trackable device for issuing a control signal to the associated trackable device for controlling the operation of the associated trackable device on the basis of the control data.

19. The system according to claim 17, wherein the associated trackable device comprises an adjustable support structure.

20. The system according to claim 19, wherein the adjustable support structure is an articulated support arm, holding a medical instrument for conducting a medical procedure, wherein the at least one computer is operably coupled to the adjustable support structure for issuing a control signal to the adjustable support structure for controlling, on the basis of the control data, the operation of the adjustable support structure.

* * * * *